(12) United States Patent
Osborn, III et al.

(10) Patent No.: US 6,206,867 B1
(45) Date of Patent: Mar. 27, 2001

(54) TAMPON WITH FLEXIBLE PANELS

(75) Inventors: Thomas W. Osborn, III, Cincinnati; Jerry E. Carstens, West Chester, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/287,994

(22) Filed: Apr. 8, 1999

Related U.S. Application Data

(63) Continuation-in-part of application No. 09/177,221, filed on Oct. 22, 1998, which is a continuation-in-part of application No. 09/124,407, filed on Jul. 29, 1998, which is a continuation-in-part of application No. 09/124,351, filed on Jul. 29, 1998, now Pat. No. 6,095,998.

(51) Int. Cl.$^7$ ...................................................... A61F 13/15
(52) U.S. Cl. ...................................... 604/385.18; 604/904
(58) Field of Search .............................. 604/904, 385.17, 604/385.18, 363

(56) References Cited

U.S. PATENT DOCUMENTS

| | | | |
|---|---|---|---|
| 3,371,666 | * | 3/1968 | Lewing ................................. 604/904 |
| 3,431,909 | | 3/1969 | Krusko . |
| 3,593,715 | * | 7/1971 | Merrill ................................. 604/904 |
| 3,618,605 | | 11/1971 | Glassman . |
| 4,212,301 | | 7/1980 | Johnson . |
| 4,627,849 | * | 12/1986 | Walton et al. ........................ 604/904 |
| 5,273,521 | * | 12/1993 | Peiler et al. .......................... 604/904 |
| 5,403,300 | * | 8/1995 | Howarth ............................... 604/904 |
| 5,549,777 | * | 8/1996 | Langdon et al. ................. 156/244.18 |
| 5,584,827 | * | 12/1996 | Korteweg et al. .................... 604/904 |
| 5,592,725 | * | 1/1997 | Brinker ................................. 604/904 |
| 5,624,423 | * | 4/1997 | Anjur et al. .......................... 604/379 |
| 5,817,077 | * | 10/1998 | Foley et al. .......................... 604/904 |
| 5,911,712 | * | 6/1999 | Leutwyler et al. ................... 604/904 |
| 6,036,666 | * | 3/2000 | Peiler et al. .......................... 604/904 |

* cited by examiner

Primary Examiner—Dennis Ruhl
(74) Attorney, Agent, or Firm—Matthew P. Fitzpatrick

(57) ABSTRACT

This invention relates to catamenial tampons, and more particularly to an improved tampon which has a compressed core portion and at least one flexible panel for improved coverage of the interior of the vaginal cavity and for directing fluid toward the tampon core. The tampon of the present invention combines the advantages of an absorbent material compressed to a self-sustaining form with an absorbent portion which is uncompressed and relatively flexible. This tampon has a central absorbent core having a first (insertion) end, a second (withdrawal) end disposed opposite the first end, and a side surface which extends between the first end and the second end. The central absorbent core is constructed from an absorbent material which has been compressed to a self-sustaining form. The tampon also includes at least one flexible panel which is joined to the central absorbent core along at least a portion of the side surface of the core. The flexible panel extends outwardly from the core away from this point of attachment.

20 Claims, 5 Drawing Sheets

TAMPON WITH FLEXIBLE PANELS

CROSS REFERENCE TO RELATED APPLICATIONS

This is a continuation in part of Ser. No. 09/177,221 filed on Oct. 22, 1998, and a continuation in part of Ser. Nos. 09/124,407 and 09/124,351 now U.S. Pat. No. 6,095,998 both filed on Jul. 29, 1998.

FIELD OF THE INVENTION

This invention relates to catamenial tampons, and more particularly to an improved tampon which has a compressed core portion and at least one flexible panel for improved coverage of the interior of the vaginal cavity and for directing fluid toward the tampon core.

BACKGROUND OF THE INVENTION

It has been long recognized that the internal vaginal cavity in its normal collapsed state is of much wider dimension in its transverse plane than in its vertical plane. It is equally well known that the minimum dimension of the vagina is near the introitus while the maximum dimension is near the cervix. It is desirable, therefore, when considering a tampon for catamenial use, to provide a structure which is in its initial state is of a size and/or shape to pass through the vaginal orifice without discomfort, and when once inside the vaginal cavity and beyond the restrictions of the orifice may be expanded, particularly in the lateral direction, to contact substantially all of surface of the vaginal walls from one side to the other in the vaginal cavity to prevent early bypass of the menstrual discharges from the cervix. Since the vaginal wall in its normal collapsed state is flaccid and has multiple folds and wrinkles which provide channels through which a significant portion of the menstrual fluids normally flow, it is also important that the absorbent tampon be as soft and conformable as possible, in order to conform to shape of the vaginal cavity and fit within these channels to minimize leakage.

The absorbent catamenial tampons now in general use comprise small, highly compressed, cylindrical plugs about three-eighths to one-half inch (about 1.0 cm to 1.3 cm) in diameter and from 1½ to 2½ inches in length (about 3.8 cm to 6.4 cm). Because of the need for absorbent capacity, they are usually formed from batts much larger in size than the vaginal orifice, and compressed to the small size indicated above in order to facilitate insertion. As fluid is absorbed, these compressed tampons are expected to re-expand toward their original pre-compressed size, and to eventually become large enough to effectively cover the vaginal cavity against fluid leakage or bypass. While it has been found that these compressed tampons perform their intended function tolerably well, even the best of them do not re-expand sufficiently, or fast enough, to provide good transverse coverage against leakage even though the vertical block may be satisfactory (although such vertical block may also be lacking). Further, most of these tampons often use only a small portion of their absorptive capacity before leakage. Since these tampons rely on some fluid absorption to re-expand, it is clear that fluid bypass and leakage can occur prematurely, and can particularly occur immediately following the time of insertion.

The prior art has long recognized that it is desirable to provide a tampon which is capable of immediately expanding after insertion, particularly in the lateral, or transverse direction. Immediate expansion of a catamenial tampon is most beneficially provided when it is not dependent on the absorption of bodily fluids for such expansion. "Dry expanding" is a term frequently used in the art to describe such a tampon.

Numerous attempts have been made to solve the problems described above with respect to a compressed cylindrical tampon through the use of a dry-expanding tampon. Some of these approaches focused on the applicator and others focused on the tampon itself.

For example, some approaches in the patent art suggest a tampon with a built-in mechanical expansion means, a typical example being U.S. Pat. No. 3,706,311 to Kohx et al. However, while a good transverse block appears to be produced, the mechanical expansion means disclosed in that patent is in the form of a flat springlike element which after insertion permanently maintains the spread configuration of the tampon, may make it difficult to remove.

Another approach is described in U.S. Pat. No. 3,512,528 to Whitehead et al, which teaches the use of a sack of absorbent material collapsed to a small size for insertion and which after insertion is expanded by the introduction of a gas or a fluid internally of the sack. The multiple steps and complicated manipulation of the gas or fluid introduction means required when using this type of tampon detract from what otherwise appears to be an effective solution of the problem.

Still another approach is described in U.S. Pat. No. 3,857,395 issued to Johnson, et al. The Johnson, et al. patent teaches the use of an elongated inserter device over which a flat tampon is draped. The inserter is said to permit the draped portion of the tampon to be pulled, rather than pushed into the cavity from the point at which the tampon is supported on the leading end of the inserter. The inserter means is equipped with a bilateral expansion mechanism which at the user's option may be operated to transversely spread the tampon at the time of insertion. The inserter device described in the Johnson, et al. patent suffers from many drawbacks, however. The Johnson inserter device is a complicated device comprising a pair of hinged arms that are capable of laterally diverging at a hinge or joint. The angular nature of the hinged arms would make that inserter uncomfortable to use. The complex nature of the hinged arms would also make it difficult and expensive to manufacture. As a result, it would not be suitable as a disposable applicator.

The prior art has recognized that a tampon should ideally be highly conformable and as non-rigid as possible. Such tampons, however, are difficult to insert and manipulate to an expanded position as the prior art attempts described above demonstrate. Therefore, all prior art attempts to provide a dry-expanding tampon have either required a complicated, cumbersome, and potentially uncomfortable application system, or have been constructed of a semi-rigid tampon or a tampon with a mechanical expansion mechanism.

Another series of attempts to overcome the problems associated with conventional, highly compressed, fluid expanding tampons is described in U.S. Pat. No. 3,749,094 issued to Duncan and U.S. Pat. Nos. 3,794,029 and 3,766,921 both issued to Dulle. The Duncan and Dulle devices are all generally conical and are designed to be dry-expanding. While these devices would be expected to overcome some of the problems associated with highly compressed, fluid expanding tampons, the Duncan and Dulle devices still require significant rigidity and compression in order to permit their use in a conventional "tube and plunger" type applicator for which they are designed. Such tampons are also constructed of absorbent polyurethane foam to provide the required inherent "spring."

It is desirable to provide a catamenial tampon which may be constructed of materials such as rayon and cotton which have long been used in the art for absorption of menstrual and other vaginal discharges. Such materials are accepted as safe and effective for such in-vivo application, are readily available, and are sufficiently inexpensive for disposable product application. It is also desirable to design a tampon which may be inserted digitally or through the use of conventional "tube and plunger" applicators since such applicators are well accepted by consumers and are easy and inexpensive to manufacture. It is also desired to provide a tampon in which at least a portion of the tampon is dry expanding to immediately cover a significant portion of the vaginal interior. Such dry expanding portion should be highly flaccid and conformable to conform to the surface of the vaginal interior.

The present invention seeks to combine the benefits of a conventional tampon comprised of an absorbent material compressed to a self-sustaining form, with the benefits of a dry-expanding tampon. One previous attempt to provide such a tampon is described in U.S. Pat. No. 4,212,301 issued to Johnson. The Johnson patent describes a digital tampon which has a portion made of absorbent material which is compressed to a self-sustaining form. An upper portion of the Johnson device is left uncompressed to provide a finger drape during digital insertion. While the Johnson device appears to combine some of the benefits of a conventional compressed tampon with the benefits of leaving an uncompressed portion, the Johnson device still suffers from some significant drawbacks. Portions of the Johnson device which are uncompressed, and therefore, potentially dry expanding are attached only to the top of the compressed portion. This restricts ability of the uncompressed portion to direct acquired fluid into the "core" portion of the tampon for long-term storage. Indeed, it appears from the Johnson disclosure, that the uncompressed portions serve to function as finger shields during insertion rather than as the unique fluid acquisition aids of the present invention.

SUMMARY OF THE INVENTION

This invention relates to catamenial tampons, and more particularly to an improved tampon which has a central absorbent core having a first end, a second end disposed opposite the first end, and a side surface which extends between the first end and the second end. The first end of the central absorbent core corresponds to an insertion end of the tampon. The side surface is oriented in a direction which is generally parallel to a longitudinally-extending central axis of the tampon. The central absorbent core is constructed from an absorbent material which has been compressed to a self-sustaining form. The tampon further comprises at least one flexible panel which is joined to the central absorbent core along at least a portion of the side surface of the core. The flexible panel extends outwardly from the core away from this point of attachment. The tampon also comprises a withdrawal cord which is attached to the tampon and extends therefrom.

In one embodiment, the flexible panel or panels may be generally rectangular. Alternatively, the flexible panel or panels may be triangular, semicircular, or trapezoidal in shape.

In one embodiments the tampon may have between 2 and 20 flexible panels. In particularly preferred embodiments, the tampon may have between 2 and 4 flexible panels.

The withdrawal core, in one embodiment may be attached to the central absorbent core of the tampon. The attachment may be at the first end of the central absorbent core in one embodiment, or may be at the second end of the central absorbent core in other embodiments. The withdrawal cord may also be attached to a flexible panel to allow for manipulation of the panel as well as ultimate withdrawal of the tampon. In additional embodiments, multiple cords may be attached to the tampon allowing for both withdrawal and post-insertion manipulation of the tampon.

In one preferred embodiment, the flexible panel or panels are at least partially absorbent. In preferred embodiments, the flexible panel or panels are provided with a driving mechanism which diverts fluid toward the central absorbent core of the tampon. In particularly preferred embodiments, this driving mechanism is provided though the use of capillary channel fibers, an osmotic driving force, or a hydrophilicity gradient, or some combination of these.

The tampon may preferably be constructed of rayon or cotton or some combination of these.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which like numerals refer to like elements and in which:

DETAILED DESCRIPTION OF THE INVENTION

This invention relates to catamenial tampons, and more particularly to an improved tampon which has a compressed core portion and at least one flexible panel for improved coverage of the interior of the vaginal cavity and direction of acquired fluid to the tampon core.

Figure 1:
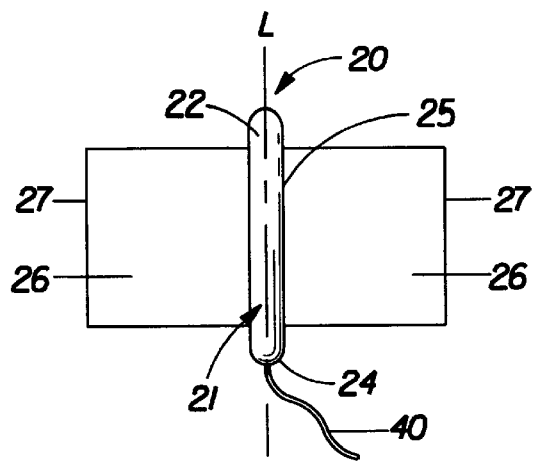
FIG. 1 is a front view of a tampon of the present invention with a compressed absorbent core and a pair of flexible side panels.

FIG. 1 shows one embodiment of the tampon of the present invention, tampon 20. As shown in FIG. 1, the tampon 20 generally comprises a conventional compressed absorbent core 21, and at least one flexible panel 26 attached to at least a portion of the side surface 25 of the tampon 26. The flexible panel 26 is capable of extending away from the absorbent core 21 at its non-attached or free end 27.

As used herein the term "tampon" refers to any type of absorbent structure which is inserted into the vaginal canal or other body cavities for the absorption of fluid therefrom. Typically, tampons are constructed from an absorbent material which has been compressed in the radial direction, the axial direction, or both, to provide a tampon which is of a size and stability to allow insertion within the vagina or other body cavity. As used herein the terms "pledget" or "tampon pledget" are intended to be interchangeable and refer to a construction of absorbent material prior to the compression of such construction into a tampon as described above. Tampon pledgets are sometimes referred to as a tampon blanks or a softwind, and the term "pledget" is intended to include such terms as well.

The absorbent core 21 of the tampon 20 shown in FIG. 1 has a first end 22 and a second end 24. The first end 22 corresponds to the insertion end of the absorbent core 21. The second end 24 corresponds to the withdrawal end of the absorbent core 21. At least one side surface 25 extends between the first end 22 and second end 24 of the absorbent core 21. The side surface 25 is generally parallel to a longitudinally extending central axis L of the absorbent core 21. The absorbent core 21 may be compressed into a generally cylindrical configuration in the radial direction or in both the radial and axial directions. In such an instance, the absorbent core 21 will have one side surface 25 which is the side of the generally cylindrical absorbent core 21.

The absorbent core 21 may be compressed into other configurations other than a cylindrical one. These may include shapes having a cross section which may be described as rectangular, triangular, trapezoidal, semi-circular, or other suitable shapes. In such configurations, the absorbent core 21 may have more than one side surface 25 as dictated by its shape.

Figure 2:
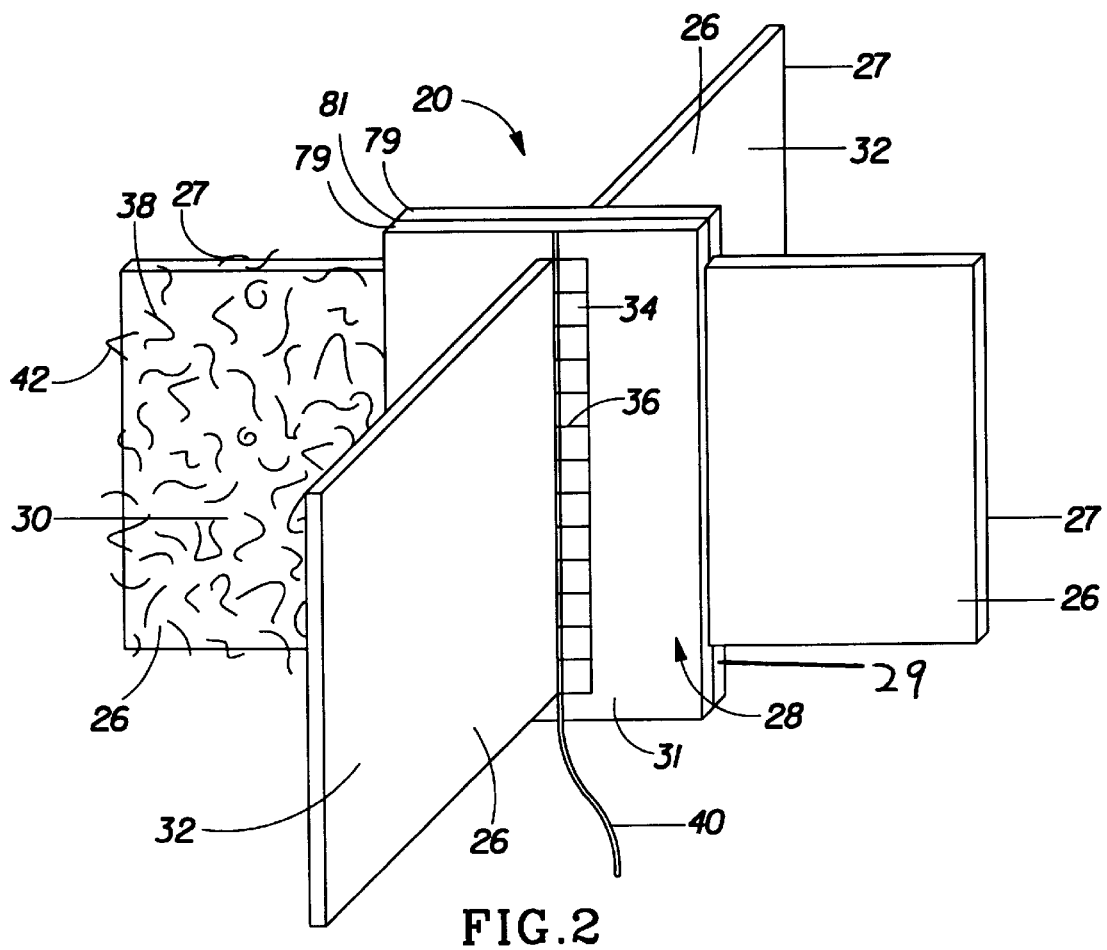
FIG. 2 is a front view of a tampon of the present invention prior to the compression of the absorbent core and showing texturing elements on one of the flexible side panels.

The absorbent core portion 21 of the tampon 20 of the present invention may be formed from any suitable tampon pledget, such as tampon pledget 28 shown in FIG. 2. Typically, the flexible panel 26 or panels are attached to the pledget 28 prior to compression of the pledget 28 to form the absorbent core 21. While this method of construction is preferred, in some variations it may be desirable to attach one or more flexible panel 26 to a side 25 of the absorbent core 21 after such core has already been compressed to a self-sustaining form. Preferably, however, the fished tampon (such as that shown in FIG. 1) may be formed by compression of the pledget 28 shown in FIG. 2 to a self-sustaining form, while leaving at least one flexible side panel 26 in an uncompressed state. The tampon pledget 28 portion of the tampon 20 which will be compressed to form the absorbent core 21 may be any suitable shape, size, material, or construction. In the embodiment shown in FIG. 2, pledget 28 is a batt of absorbent material which is a generally rectangular pad of absorbent material.

While the pledget 28 shown in FIG. 2 is generally rectangular, other shapes such as trapezoidal, triangular, hemispherical, and chevron shaped are also acceptable. The pledget 28 may be a laminar structure comprised of integral or discrete layers. In one embodiment, the pledget 28 may comprise outer layers 79 and at least one intermediate layer 81 positioned between the outer layers 40. In other embodiments, the pad need not have a layered structure at all. The pledget 28 may comprise a folded structure, may be rolled, may comprise a "petal" structure or any other of the structures which are known in the art with respect to tampon pledgets.

The pledget 28, and consequently, the resulting absorbent core 21 of the tampon 20 may be constructed from a wide variety of liquid-absorbing materials commonly used in absorbent articles such as rayon, cotton, or comminuted wood pulp which is generally referred to as airfelt. Examples of other suitable absorbent materials include creeped cellulose wadding; meltblown polymers including conform; chemically stiffened, modified or cross-linked cellulosic fibers; synthetic fibers such as crimped polyester fibers; peat moss; tissue including tissue wraps and tissue laminates; or any equivalent material or combinations of materials, or mixtures of these. Preferred absorbent materials comprise cotton, rayon (including tri-global and conventional rayon fibers, and needle punched rayon), folded tissues, woven materials, nonwoven webs, synthetic and/or natural fibers. The tampon 20 and any component thereof may comprise a single material or a combination of materials. Additionally, superabsorbent materials, such as superabsorbent polymers or absorbent gelling materials may be incorporated into the tampon 20.

In the preferred embodiment shown in FIGS. 1 and 2, the pledget 28 and resulting absorbent core 21 is formed of a soft absorbent material such as rayon, cotton (including either long fiber cotton or cotton linters) or other suitable natural or synthetic fibers or sheeting. The materials for the tampon 26 can be formed into a fabric, web, or batt that is suitable for use in the pledget 28 by any suitable process such as airlaying, carding, wetlaying, or other known techniques.

In one non-limiting preferred embodiment, the tampon pledget 28 and resulting absorbent core 21 comprise rayon, cotton, or combinations of both materials. The rayon used in the tampon pledget 28 may be any suitable type typically used in disposable absorbent articles intended for in vivo use. Such acceptable types of rayon include GALAXY Rayon (a tri-lobed rayon structure) available as 6140 Rayon from Courtaulds Fibers Ltd., of Hollywall, England. SARILLE L rayon (a round fiber rayon), also available from Courtaulds Fibers Ltd. is also suitable. Any suitable cotton material may be used in the tampon pledget 28. Suitable cotton material includes, long fiber cotton, short fiber cotton, cotton linters, T-fiber cotton, card strips, and comber cotton. Preferably, the cotton layers should be a scoured & bleached cotton absorbent with a glycerin finish, a lemolin finish, or other suitable finish.

The absorbent material of the pledget 28 may be surrounded with a liquid permeable overwrap material, if desired. Such overwrap materials may comprise rayon, cotton, bicomponent fibers, or other suitable natural or synthetic fibers known in the art. If the pledget 28 of the present invention is layered, the layers may comprise different materials. For example, the outer layers 79, may comprise primarily rayon, while the intermediate layer 81 or layers may comprise primarily cotton. Optionally, the entire pledget 28 may comprise a uniform or non-uniform blend of materials throughout.

The pledget 28 may be any suitable size and thickness suitable for compression into a tampon having a size similar to those of conventional currently available tampons. A typical size for such pledgets may be about 3½ inches in length and about 1¾ inches in width. One preferred range for the overall basis weight is from about 150 g/m² to about 750 g/m².

Figure 7:
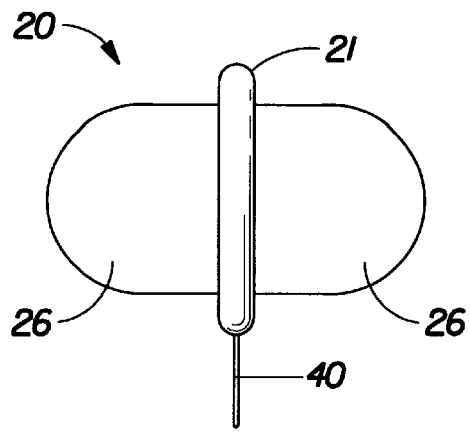
FIG. 7 is a front view of one embodiment of a tampon of the present invention having flexible panels with a semi-circular portion.
Figure 8:
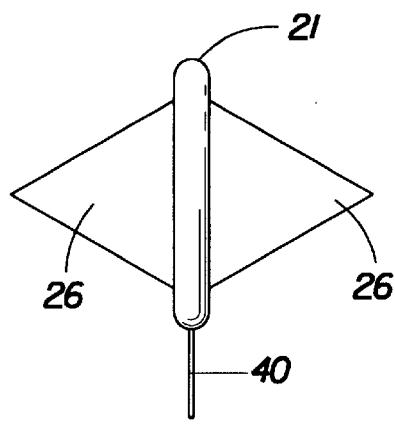
FIG. 8 is a front view of one embodiment of a tampon of the present invention having triangular flexible panels.
Figure 9:
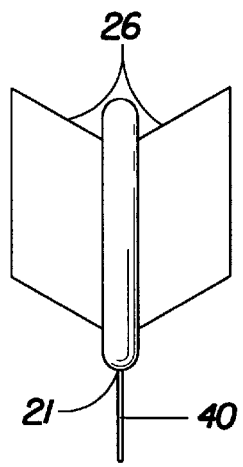
FIG. 9 is a front view of one embodiment of a tampon of the present invention showing an alternative shape of the flexible panels.

The tampon 21 of the present invention is also provided with at least one flexible panel 26 attached to a side surface 25 of the absorbent core 21. In the embodiment shown in FIGS. 1 and 2, the flexible panels 26 are generally rectangular in shape. Other shapes are also possible for the flexible panels 24 or portions thereof such as semi-circular (shown, e.g., in FIG. 7), trapezoidal (e.g. FIG. 10), or triangular (e.g. FIG. 8).

Figure 17:
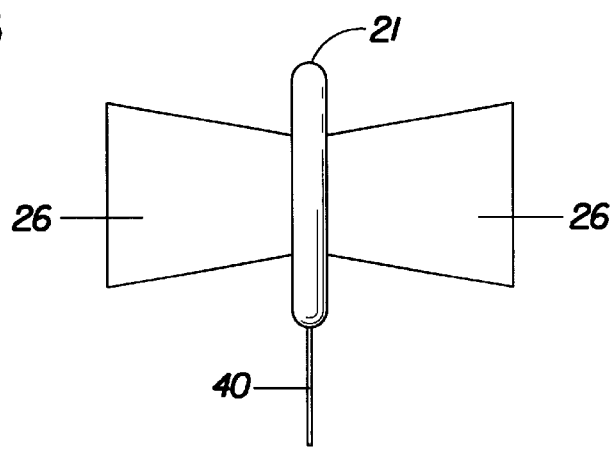
FIG. 17 is a front view of an alternative embodiment of a tampon of the present invention showing an alternative shape of the flexible extensions.

The flexible panels 26 preferably have a length which is about 50% to about 90% of the length of the absorbent core 21. While the flexible panels 26 preferably have a length (measured in the axial direction) which is shorter than the length of the absorbent core 21, they may have a length which is longer than that of the absorbent core 21. The length of the flexible panels 26 need not be uniform from the attachment end of the panel 26 to the free end 27 of the panel 26. FIG. 17, for example, shows one embodiment in which the length of the flexible panels 26 is non-uniform. Many other such non-uniform length embodiments are also possible.

Figure 10:
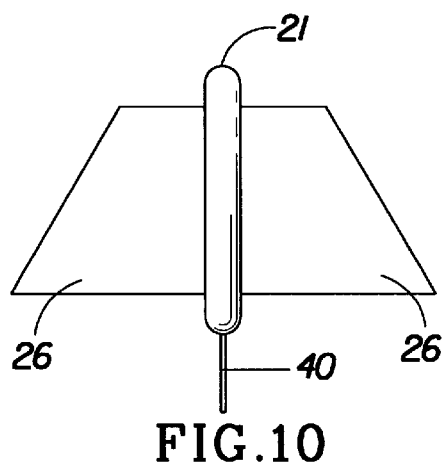
FIG. 10 is one embodiment of a tampon of the present invention having trapezoidal flexible panels.
Figure 11:
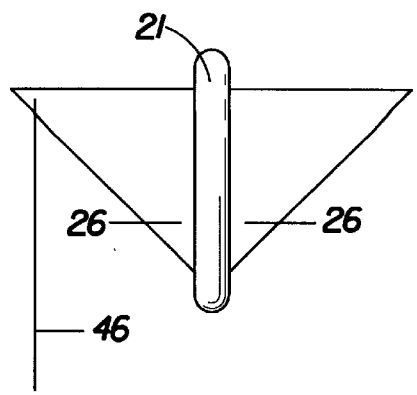
FIG. 11 is one embodiment of a tampon of the present invention having a withdrawal cord attached to one of the flexible panels.
Figure 12:
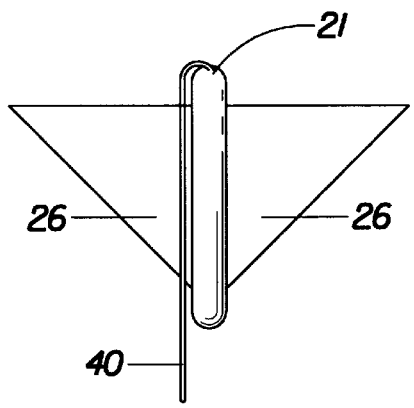
FIG. 12 is a front view of an embodiment of a tampon of the present invention in which the withdrawal cord is attached to the insertion end of the absorbent core.

The width of each flexible panel 26 refers to the distance from the attachment of the panel 26 to a side edge 25 of the absorbent core 21 to the unattached (or free) end 27 of the panel 26 (which end is sometimes also referred to as the "distal" end). The width of each flexible panel 26 or panels is preferably about 2 mm to about 30 mm, more preferably from about 3 mm to about 25 mm, most preferably from about 5 mm to about 20 mm. The width of a given flexible panel 26 need not be uniform along its length. FIGS. 10–12, for example, show some possible embodiments in which the width of the flexible panels 26 is not uniform along their length.

The caliper of the flexible panel 26 or panels 26 is preferably less than or equal to about 3 mm, more preferably less than or equal to about 2 mm, and most preferably less than or equal to about 1 mm. Caliper measurements given herein were measured using an AMES gage with a 0.25 psig load and a 0.96 inch diameter foot. Those skilled in the art will recognize that if a 0.96 inch diameter foot is not appropriate for a particular sample size, the foot size may be varied while the load on the gauge is accordingly varied to maintain a confining pressure of 0.25 psig.

The flexible panels 26 may be constructed from any suitable material. The materials listed above which are suitable for use in the absorbent core 21 are also acceptable for use in the flexible panels 26. The flexible panels 26 may be constructed of a tissue layer or layers. One suitable tissue is an airlaid tissue available from Fort Howard Tissue Company of Green Bay, Wisconsin, and having a basis weight of about 35 lbs./3000 sq. ft. Another suitable airlaid tissue is available from Merfin Hygenic Products, Ltd., of Delta, British Columbia, Canada, having a basis weight of about 61 lbs./3000 sq. ft. and having the designation grade number 176.

Figure 3:
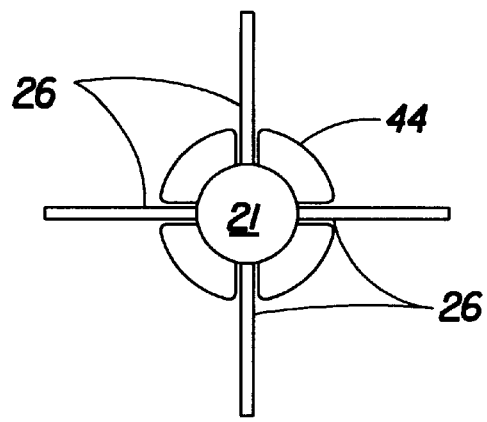
FIG. 3 is a top view showing one manner in which the absorbent core of the tampon of the present invention may be compressed.

One preferred embodiment for the construction of the tampon 20 of the present invention is shown in FIGS. 1–3. This example is given by way of illustration only, and one skilled in the art will readily appreciate that a variety of options may be employed to construct a tampon of the present invention as defined in the appended claims. The tampon 20 shown in FIG. 2 comprises four flexible panels 26. The tampon pledget 28 is a rectangular batt of material which has two major surfaces 31 and two side surfaces 29. In the embodiment shown in FIG. 2, there are flexible panels 26 attached to the pledget 28 which are oriented in directions which are parallel and perpendicular to the major surfaces 31 of the pledget 28. As shown in FIG. 2, if the tampon is to be provided with a pair of flexible panels 26 oriented in a direction which is generally parallel to the major surfaces 31 of the pledget 28, a single piece of flexible panel material may be used. This material may extend through the interior of the pledget 28 or may be attached to either major surface 28 of the pledget. Of course, it is not necessary that a single piece of material extend all the way through or across the pledget 28, and a pair of flexible panels 26 may be individually attached to the pledget 28.

FIG. 2 also shows a pair of flexible panels 26 each of which are attached to the pledget 28 in a direction which is generally perpendicular to the major surfaces 31 of the pledget 28. In such a construction, each panel 26 may be individually attached to the pledget, as shown in FIG. 2. For example, at attachment tab 34 may be employed for such purpose. Any suitable attachment mechanism such as stitching 36 may be used to attach the tab 34, and consequently, the panels 26 to the pledget 28.

The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element; i.e., one element is essentially part of the other element.

The flexible panels 26 may be joined to the pledget 26 and to the resulting absorbent core 21 (or directly to the preformed absorbent core) by any variety of means. For example, the flexible panels 26 may be joined to the pledget 28 using any suitable adhesive. Such adhesive may extend continuously along the length of attachment or it may be applied in a "dotted" fashion at discrete intervals. Alternatively, the flexible panels 26 may be joined to the pledget 28 by stitching (such as stitching 36). Such stitching may use cotton or rayon thread. Other attachment mechanisms include thermally bonding (for example where the tampon core and panels have thermally bonded fibers or other thermally bonding materials incorporated therein), fusion bonding, or any other suitable means known in the art for joining such materials.

The flexible panels 26 are attached to the side 25 of the absorbent core 21 of the tampon 20 and extend outwardly therefrom to a free end 27 which is unattached to the absorbent core 21. The flexible panels 26 may be biased slightly outward from the absorbent core 21 so as to tend to keep the panels 26 in contact with the inner surfaces of the vagina when the tampon 20 is in place. Additionally, the naturally moist surfaces of the vagina will have a tendency to adhere to the material comprising the flexible panels 26 further tending to keep them in contact with the surfaces of the vagina. Preferably, the flexible panels 26 should be capable of a wide range of motion which is independent of other flexible panels 26 which may be present in the tampon 20.

The flexible panels 26 may be either absorbent or non-absorbent. Preferably, the flexible panels 26 have at least some absorbency. The flexible panels 26 may have an advancing contact angle greater than the advancing contact angle of the absorbent core 21, such that fluid is preferentially directed toward and absorbed by the absorbent core 21. Optionally, the flexible panels 26 may be treated to make them less absorbent than the absorbent core 21. Preferably, the majority of the fluid absorbed and retained by the tampon 20 will ultimately be retained in the absorbent core 21. For a more detailed description of hydrophilicity and contact angles see the following publications which are incorporated by reference herein: The American Chemical Society Publication entitled "Contact Angle, Wettability, and Adhesion," edited by Robert F. Gould, and copyrighted in 1964; and TRI/Princeton Publications, Publication Number 459, entitled "A Microtechnique for Determining Surface Tension," published in April 1992, and Publication Number 468 entitled, "Determining Contact Angles Within Porous Networks," published in January, 1993, both edited by Dr. H. G. Heilweil.

The major surface the flexible panel 26 or panels may be plain, or it can be textured. It is also acceptable in embodiments with multiple to panels 26 to have both textured and non-textured panels (such as shown in FIG. 2 in which only one panel 26 is provided with texturing elements 38). Preferably, the flexible panels 26 are provided with texturing elements 38 and in more preferred embodiments, all of the flexible panels 26 are provided with such texturing elements 38.

As noted above, an example of such a flexible panel 26 with a textured surface is shown in FIG. 2. The texturing can be provided through a variety of means, including a multiplicity of texturing elements 38 as is shown in FIG. 2. Such texturing may be provided by needle punching the surface of the flexible panel 26 to be textured. Additionally, the texturing elements 38 may be attached to either or both surfaces of a given flexible panel 26. Individual texturing elements 28 can be passed through the flexible panel 26 to extend outwardly from either major surface. Additionally, individual texturing elements 38 may be attached to an intermediate location between the major surfaces of a given flexible panel 26 or any combination of these locations.

The flexible panels 26 preferably have major surfaces which comprises a plush or terry cloth type fabric which has a plurality of texturing elements 38 (such as outwardly extending fibers) extending outwardly therefrom. The texturing elements 38 may be randomly oriented or may be aligned in a particular direction or directions. Preferably these texturing elements 38 are generally perpendicular to the surfaces of the flexible panels 26. These texturing elements 38 penetrate into the rugosites in the vaginal cavity to intercept menses and reduce "by-pass" failures (failures from menses traveling in these rugosites and around the tampon). Preferably, the texturing elements 38 may have a tendency to flex and/or orient themselves in response to forces exerted by the vaginal surfaces.

The texturing elements 38 may be "looped" and attached to the surface of the flexible panel 26 at both ends. Suitable texturing elements may be formed from a single long fiber or a series of fibers which are punched in and out of the surface of the flexible panel 26 to form a plurality of loops. As noted, both sides, one side, or neither side of a given flexible panel 26 may be provided with texturing elements 38.

The texturing elements 38 are preferably hydrophilic so as to facilitate the ready transfer of fluid from the vaginal surfaces to the main surface of the flexible panel 26 and, ultimately, to the absorbent core 21. The texturing elements 38 may also be configured to transfer fluid from the vaginal surfaces to the main surface of the flexible panel 26 and ultimately, to the absorbent core 21 through the use of a density gradient, hydrophilicity gradients, an osmotic driving force, capilarity, or a similar mechanism. Suitable materials for use in such fluid acquisition/transfer mechanisms are rayon (including, e.g., conventional, tri-lobed or multi-lobed rayon fibers), polyethylene, polypropylene, polyester, synthetic bi-component fibers, absorbent foams and combinations thereof, all of which fibers may be used either singly or in combination with other fibers are known in the art. Capillary channel fibers are a highly preferred fiber for the texturing elements 38.

A preferred material for the flexible panels 26 is known as Cotton Interlock available from Empirical Manufacturing Co, Cincinnati, Ohio, as model no. C120. This is a textured cotton similar to a terry cloth or terry towel.

The flexible panels 26 may optionally be provided with a cleansing or lubricating composition to facilitate insertion, removal, or for other purposes. The flexible panels 26 may have, and preferably do have, an incorporated mechanism to preferentially direct acquired fluid from the flexible panel 26 to the absorbent core 21. Such a mechanism may be any of those described above with respect to the texturing elements 38.

The flexible panels 26 may be extensible or stretchable in one or more directions. This may be accomplished through the construction of flexible panels 26 from an inherently stretchable material or from a laminate where one or more of the layers is stretchable or extensible. Additionally, the material comprising the flexible panels 26 may be made extensible by a suitable mechanical process such as ring rolling or corrugating. The flexible panels 26 may also incorporate an extensible strip or element.

The flexible panels 26 should have a strength and stiffness which make them both comfortable and able to dynamically adjust to the motion of the vagina. Preferably, the flexible panels 26 have sufficient strength to prevent them from shredding and/or breaking which may leave pieces remaining in the wearer's vagina upon removal of the tampon 20. Similarly, the flexible panels 26 should have sufficient flexibility to dynamically adjust to the motion of the vagina.

A withdrawal cord 40, examples of which are shown in FIGS. 1–2, is typically attached to the tampon 20 for removal of the tampon after use. The withdrawal cord 48 may be attached in any suitable manner known in the art including sewing, adhesive attachment, or a combination of known bonding methods. The withdrawal cord 40 may be absorbent or non-absorbent, and is preferably non-absorbent. The withdrawal cord 40 may be attached to any suitable location on the tampon 20. In the embodiment shown in FIGS. 1–2, a single withdrawal cord 40 is attached to the second end 24 of the absorbent core 21. The withdrawal cord 40, is typically attached to the tampon pledget 28 while the pledget 28 is still uncompressed as shown in FIG. 2. The withdrawal cord 40 may be attached along the entire length one major surface of the pledget 28 and hang free from one end, such as the second end 24.

In one variation of the tampon of the present invention, the tampon may be provided with a flexible panel attached withdrawal cord 46, such as shown in FIG. 11. In other words, the withdrawal cord 26 may be attached to any suitable location on one of the flexible panels 26. Preferably, such a panel attached withdrawal cord 26 is attached proximate the free end of the flexible panel 26.

FIG. 12, shows another variation in which the withdrawal cord is attached to the absorbent core 21 portion of the tampon, but is attached to the first end 22 (or insertion end). Such an attachment location allows the user to pull on the withdrawal cord 40 after insertion of the tampon for post-insertion rotation or other manipulation. Some users will prefer the tampon to be disposed in a generally horizontal relationship in the vaginal canal rather than a primarily vertical one. Additionally, some users will use an insertion end attached withdrawal cord 40 to completely rotate the tampon post insertion. Such complete rotation may assist the flexible panels 26 in extending to more effectively cover the surfaces of the vaginal interior.

Figure 13:
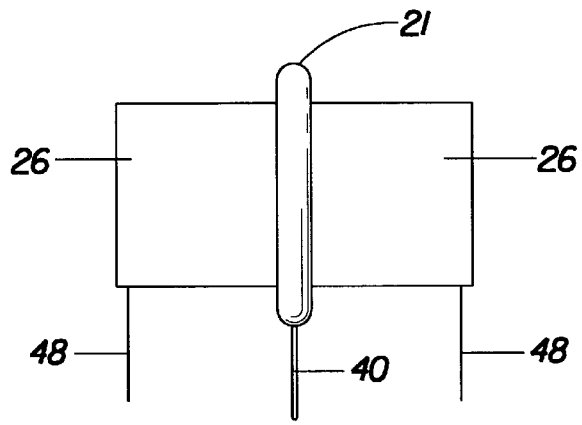
FIG. 13 is a front view of a tampon of the present invention having the main withdrawal cord attached to the compressed core and having flexible panel manipulation cords.
Figure 14:
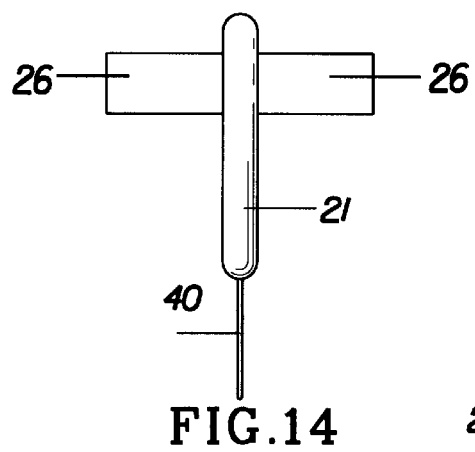
FIG. 14 is a front view of an alternative embodiment of a tampon of the present invention.
Figure 15:
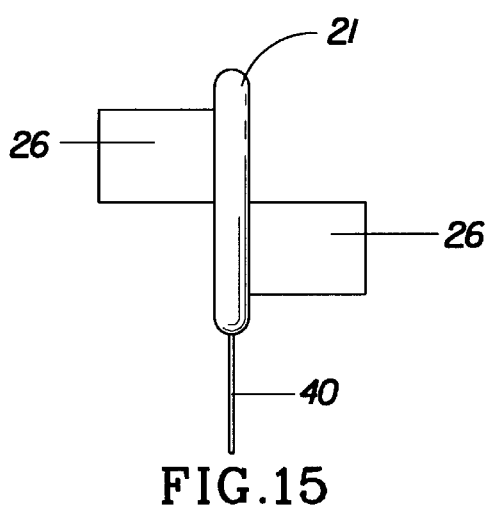
FIG. 15 is a front view of an alternative embodiment of a tampon of the present invention having offset flexible extensions.
Figure 16:
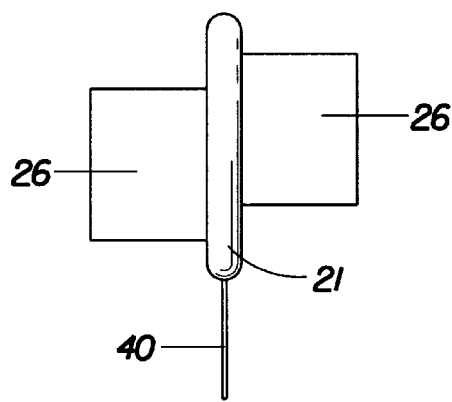
FIG. 16 is a front view of an alternative embodiment of a tampon of the present invention having partially offset flexible extensions.

The tampon of the present invention may also be provided with flexible panel manipulation cords 48 such as shown in FIG. 13. While such panel manipulation cords are optional, any flexible panel 26 provided on the tampon may have a cord attached to any suitable location. Such cords may be used by the user to control the movement of the flexible panels 26 after insertion of the tampon itself.

To form a tampon ready for use, the tampon pledget 28 is typically compressed and heat conditioned in any suitable conventional manner. Pressures and temperatures suitable for this purpose are well known in the art. Typically, the pledget 28 is compressed in both the radial and axial direction using any means well known in the art. While a variety of techniques are known and acceptable for these purposes, a modified tampon compressor machine available from Hauni Machines, Richmond, Va, is suitable. Preferably, the flexible panels 26 are attached to the uncompressed pledget 28 as shown in FIG. 2. The pledget 28 may then be compressed into the absorbent core 21 as shown in FIG. 3. FIG. 3 shows a series of compression dies 44 provided with narrow axial slits which allow compression of the absorbent core 21 without compressing the flexible panels 26. It may also be desirable in some embodiments to attach the flexible panels 26 to the absorbent core 21 after compression of such absorbent core.

The tampon 20 of the present invention may be inserted digitally or through the use of an applicator. If the tampon 20 is to be used for digital insertion, it may be desirable to form the pledget from a layer of absorbent material which has been rolled into a cylindrical shape. Flexible panels 26 could be attached to such a layer in any suitable manner. For example, the attachment tabs 34 shown in FIG. 2 may be used to attach one or more flexible panels 26 to a rolled pledget.

Any of the currently available tampon applicators may also be used for insertion of the tampon of the present invention. Such applicators of typically a "tube and plunger" type arrangement and may be plastic, paper, or other suitable material. Additionally, a "compact" type applicator is also suitable. The flexible nature of the flexible panels 26 allows them to reside with the tampon in the applicator tube along with the absorbent core 21 portion of the tampon. The applicator plunger will push the absorbent core 21 out of the applicator due to the compressed nature of the core. The flexible extensions 26 are then available to begin collecting fluid immediately after insertion from their generally uncompressed state.

Figure 4:
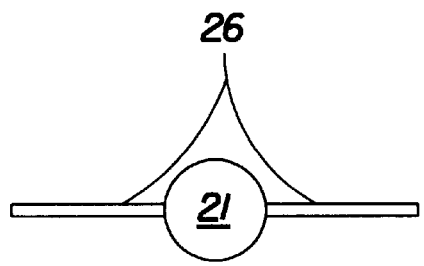
FIG. 4 is a top view of one embodiment of a tampon of the present invention having two flexible panels.
Figure 5:
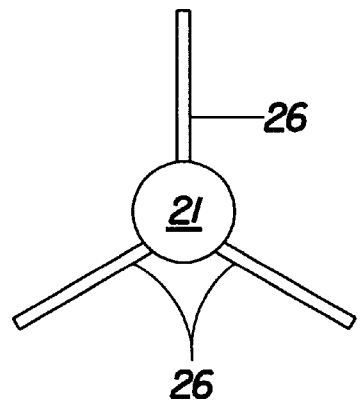
FIG. 5 is a top view of one embodiment of a tampon of the present invention having three flexible panels.
Figure 6:
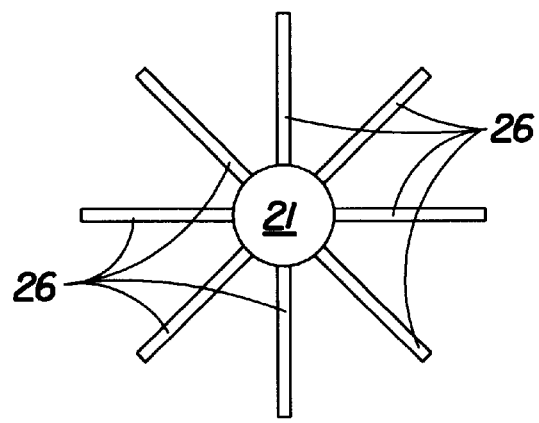
FIG. 6 is a top view of one embodiment of a tampon of the present invention having eight flexible panels.

As noted, the tampon of the present invention has at least one flexible panel 26. Preferably, between 2 and 4 flexible panels 26 are present. FIG. 4 shows one example of a tampon of the present invention having two panels. FIG. 5 shows three such flexible panels. FIG. 6 shows an embodiment having eight flexible panels 26. Preferably, the panels 26 are approximately evenly spaced around the absorbent core 21 although this is not required. FIGS. 7–10 and 14–17 show a variety of examples of the variations which are possible for the flexible extensions 26. These examples are not exhaustive and other variations are also possible.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

The disclosures of all patents and patent applications referred to in this specification (including those listed in the Cross Reference to Related Applications Section) are hereby incorporated by reference as if fully set forth herein. While particular embodiments of the present invention have been illustrated and described, it would be obvious to those skilled in the art that various other changes and modifications can be made without departing from the spirit and scope of the invention.

What is claimed is:

1. A catamenial tampon having a length oriented in an axial direction said tampon comprising:

a central absorbent core having a first end, a second end disposed opposite said first end, and a side surface extending between said first end and said second end, wherein said first end corresponds to an insertion end of said tampon, said side surface being oriented in a direction generally parallel to a longitudinally-extending central axis, said central absorbent core being constructed from an absorbent material compressed to a self-sustaining form;

at least one flexible panel joined to said central absorbent core along at least a portion of said side surface, said at least one flexible panel extending outwardly from said central absorbent core to a free end, said at least one flexible panel having a length oriented in said axial direction, and having a width extending from said side surface to said free end and oriented in a direction perpendicular to said length, and having a thickness oriented in a direction perpendicular to both said length and said width wherein said width of said at least one flexible panels exceeds said thickness of said at least one flexible panel wherein said at least one flexible panel has a first density and said central absorbent core has a second density said second density being greater than said first density; and and a withdrawal cord joined to said tampon and extending therefrom.

2. The tampon of claim 1 wherein said at least one flexible panel is generally rectangular.

3. The tampon of claim 1 wherein said tampon comprises between 2 and 20 flexible panels.

4. The tampon of claim 3 wherein said tampon comprises between 2 and 4 flexible panels.

5. The tampon of claim 1 wherein said at least one flexible panel is generally triangular.

6. The tampon of claim 1 wherein said at least one flexible panel is generally semi-circular.

7. The tampon of claim 1 wherein said at least one flexible panel is generally trapezoidal shaped.

8. The tampon of claim 1 wherein said withdrawal cord is attached to said central absorbent core.

9. The tampon of claim 8 wherein said withdrawal cord is attached to said first end of said central absorbent core.

10. The tampon of claim 8 wherein said withdrawal cord is attached to said second end of said central absorbent core.

11. The tampon of claim 1 wherein said withdrawal cord is attached to one of said at least one flexible panel thereby allowing said withdrawal cord to also be used for manipulation of said at least one flexible panel.

12. The tampon of claim 1 further comprising a second cord attached to said tampon in addition to said withdrawal cord wherein at least one of said withdrawal cord and said second cord are capable of being used for post insertion manipulation of said tampon.

13. The tampon of claim 1 wherein said at least one flexible panel is at least partially absorbent.

14. The tampon of claim 1 wherein said at least one flexible panel is provided with a driving mechanism to divert fluid toward said central absorbent core of said tampon.

15. The tampon of claim 14 wherein said driving mechanism is provided through the use of capillary channel fibers.

16. The tampon of claim 14 wherein said driving mechanism is provided through the use of control of capillary size.

17. The tampon of claim 16 wherein said control of capillary size is provided through the use of a density gradient.

18. The tampon of claim 14 wherein said driving mechanism is provided though the use of a hydrophilicity gradient.

19. The tampon of claim 1 wherein said tampon is comprised of rayon.

20. The tampon of claim 1 wherein said tampon is comprised of cotton.

\* \* \* \* \*